(12) United States Patent
Kinnunen et al.

(10) Patent No.: US 6,845,654 B2
(45) Date of Patent: Jan. 25, 2005

(54) METHOD FOR MEASURING THE SURFACE TENSION OF AN AQUEOUS SOLUTION

(75) Inventors: Paavo Kinnunen, Espoo (FI); Tim Söderlund, Helsinki (FI)

(73) Assignee: Kibron Inc. OY, Helsinki (FI)

( * ) Notice: Subject to any disclaimer, the term of this patent is extended or adjusted under 35 U.S.C. 154(b) by 0 days.

(21) Appl. No.: 10/416,522

(22) PCT Filed: Jan. 9, 2002

(86) PCT No.: PCT/FI02/00015

§ 371 (c)(1), (2), (4) Date: Oct. 29, 2003

(87) PCT Pub. No.: WO02/055996

PCT Pub. Date: Jul. 18, 2002

(65) Prior Publication Data

US 2004/0050148 A1 Mar. 18, 2004

(30) Foreign Application Priority Data

Jan. 12, 2001 (FI) .............................. 20010070

(51) Int. Cl.⁷ .............................................. G01N 13/02
(52) U.S. Cl. ................................................ 73/64.48
(58) Field of Search ........................................ 73/64.48

(56) References Cited

U.S. PATENT DOCUMENTS

| | | | |
|---|---|---|---|
| 4,527,421 A | * | 7/1985 | Miller, Jr. .................. 73/64.51 |
| 4,663,159 A | | 5/1987 | Brode, II et al. |
| 4,828,799 A | * | 5/1989 | Love et al. .................. 422/70 |
| 5,792,945 A | | 8/1998 | Murakami .................. 73/64.48 |
| 6,274,634 B1 | * | 8/2001 | Yasueda et al. ............. 514/781 |

FOREIGN PATENT DOCUMENTS

WO    WO 00/00815    1/2000

* cited by examiner

Primary Examiner—Daniel S. Larkin
(74) Attorney, Agent, or Firm—Armstrong, Kratz, Quintos, Hanson & Brooks, LLP

(57) ABSTRACT

The present invention is directed to a method for determining the surface activity properties of an amphiphilic substance, such as a drug, the method including a step wherein the surface tension of an aqueous solution of the said substance is measured at its air-water interface at a plurality of concentrations of said substance and determining the relationship between the surface tension and the concentration of the substance, and using the relationship so determined to predict the surface activity properties of the substance, according to which method, to the aqueous solution, a water soluble substance, which increases the surface tension of the aqueous solution is added in an amount to provide a concentration of 0.3 M up to the saturation concentration of the said substance in said solution.

13 Claims, 3 Drawing Sheets

METHOD FOR MEASURING THE SURFACE TENSION OF AN AQUEOUS SOLUTION

FIELD OF THE INVENTION

The present invention generally relates to a method for measuring the surface tension of an aqueous solution at its air-water-interface. Specifically, the object of the invention is a method for determining the surface activity properties of a substance, such as a drug, the method including a step wherein the surface tension of an aqueous solution of the said substance is measured at a plurality of concentrations of the substance, and the effect on the surface tension of the aqueous solution by the substance is determined, by determining the relationship between the surface tension and the concentration of the substance.

BACKGROUND OF THE INVENTION

The amphiphilicity and detergent properties of a substance, such as of a drug, correlate to their adsorption in the gastro-intestinal tract, to their distribution in the tissues and especially to their blood-brain barrier (BBB) permeability, liver metabolism, and urinary excretion, that is to their so-called ADME properties. One way to estimate molecular hydrophobocity is to determine the partition coefficient (log P) of the substance in octanol/water. Amphiphilicity and detergent properties have conventionally been determined by measuring the effect of the substance on the surface tension of water. The surface tension can be measured in a variety of ways, for example, in a method involving the use of a Wilhelmy plate or a du Nouy ring.

A problem relating to a majority of the substances to be used for pharmaceutical purposes and thus to be tested for their ADME properties is their poor solubility in water. For this reason, the pharmaceutical industry routinely uses a so-called base solution of the drug, which is a solution of the drug in dimethylsulfoxide (DMSO), the solution being 10 mM with respect to the drug. However, DMSO is not well suited for the use in surface tension measurements because its surface tension is low and it lowers the surface tension of water and of aqueous solutions. The 10 mM solutions of the drug in DMSO are used in undiluted form, because the changes in surface tension brought about by the substances from which the ADME properties can be evaluated, require the concentration to be varied on a micro-millimolar scale. The DMSO carried over into the system significantly reduces the signal obtained, that is the sensitivity of measurement.

Poor pharmacokinetics is currently the major reason for the failure of compounds in clinical trials. Accordingly, there is an urgent need for easy, high-throughput, and robust screening methods for pharmacokinetics. A procedure for the estimation of BBB-permeability based on the surface activity of drugs has recently been suggested (Seelig, R. et al.: A method to determine the ability of drugs to diffuse through the blood-brain barrier, *Proc. Natl. Acad. Sci. USA* 91:68–72 (1994); Fischer H. et al., Blood-brain barrier permeation: molecular parameters governing passive diffusion, *J. Membrane Biol.* 165:201–211 (1998)). However, although the predictive value of the method is excellent, the method described by these authors is slow, the measurement cycle approaching maximally four hours. Moreover, due to the large cuvette volumes needed, the consumption of compounds is high.

The present invention alleviates the disadvantages associated with the known method and provides a sensitive method for measuring the surface tension. The method allows for the screening of compounds with excellent prediction, for example, of BBB-permeability of compounds entering the central nervous system by passive diffusion. The data obtained also reveal a good correlation to the urinary excretion of the drugs, thus pointing out the common biophysical nature of some of the pharmacokinetic determinants in ADME.

SUMMARY OF THE INVENTION

An object of the invention thus is a method for determining the surface activity properties of an amphiphilic substance, such as a drug, the method including a step wherein the surface tension of an aqueous solution of the substance is measured at its air-water interface at a plurality of concentrations of said substance and determining the relationship between the surface tension and the concentration of the substance, and using the relationship so determined to predict the surface activity properties of the substance, according to which method, to the aqueous solution, a water soluble substance, which increases the surface tension of the aqueous solution is added in an amount to provide a concentration of 0.3 M up to the saturation concentration of the substance in said solution.

Preferably, the substance, the surface activity properties of which are to be determined, is a bioactive substance.

BRIEF DESCRIPTION OF THE DRAWINGS

In the enclosed drawings

DETAILED DESCRIPTION OF THE INVENTION

Figure 1:
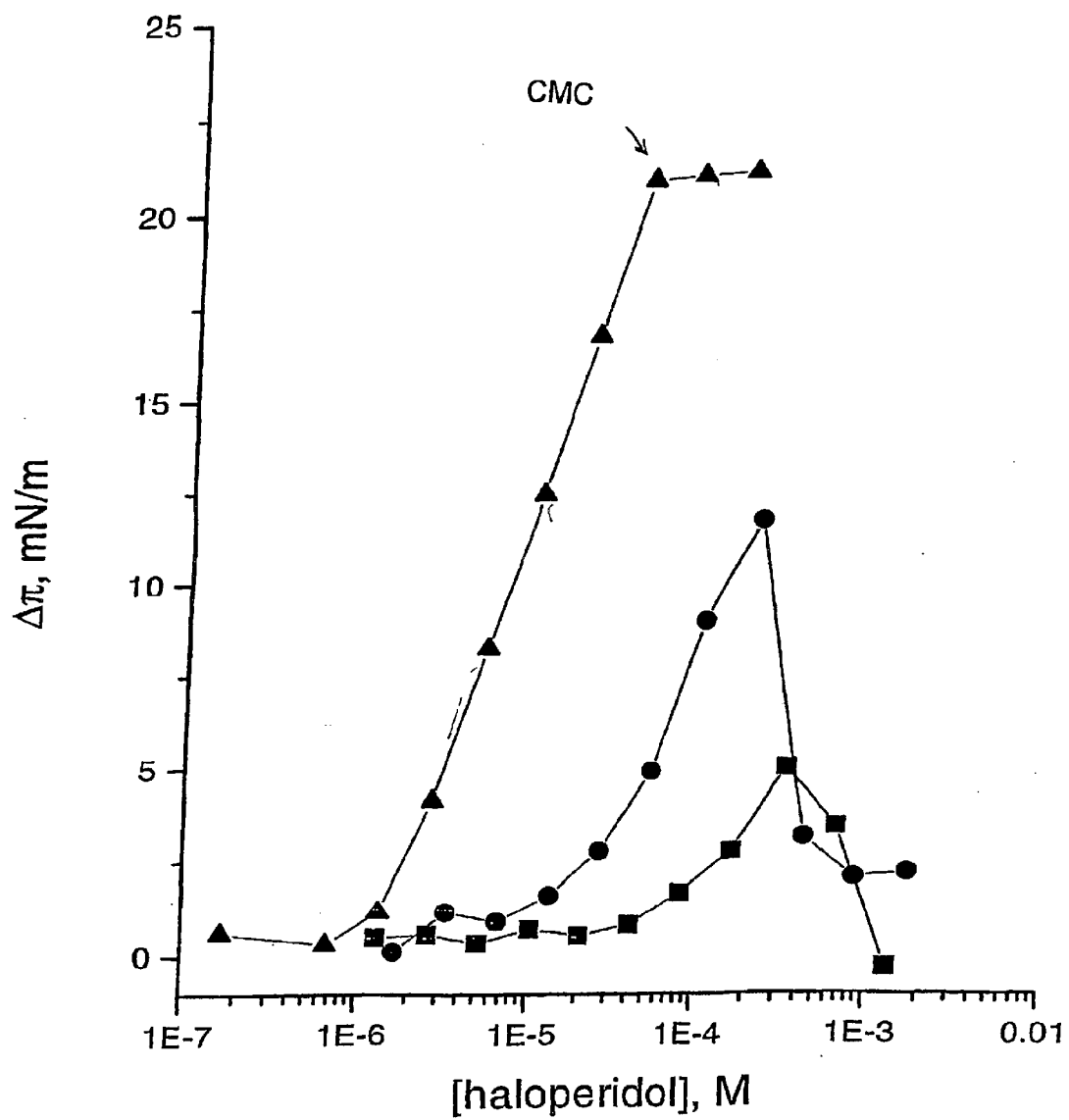
FIG. 1 shows in graphic form the surface pressure $\pi$ as a function of the logarithm of the concentration (lnC) for the drug haloperidol in a buffered (50 mM Tris-HCl, ph 8) aqueous solution containing either 4M of NaCl and 1% DMSO (▲) or 10% DMSO (●), or 114 mM NaCl and 10% (■).

According to the invention it has now been discovered that by adding, in a sufficient quantity, to the aqueous solution a water soluble substance, which as such increases the surface tension of the aqueous solution, it is possible to markedly improve the sensitivity of the system and method used. Compounds which increase the surface tension of aqueous solutions can be referred to as 'water structure makers', or as anti-chaotropic substances, see for example *Journal of Molecular Structure*, 237 (1990) 411–419, *J. Phys. Chem.* 8, 1998, 102, 7058–7066.

A typical substance for increasing the surface tension is a salt, such as an alkali- or earth alkaline metal salt, such as a halide or carbonate. A suitable salt is a chloride, such a sodium or potassium chloride. Suitable organic salts are for example carboxylic acid salts, such as glutamates, e.g. sodium glutamate, tartrates, succinates, and citrates.

Besides salts, there are also available other water soluble substances which have a surface tension increasing effect on the aqueous solution; such substances can easily be determined by a person skilled in the art. As examples of such substances, choline and betaine, sugars and polyols, e.g. mannitol, inositol, sorbitol, and xylitol, and amino acids, such as lysine, or their salts, may be mentioned. Preferably, these substances should not be efficient hydrogen bond donors or acceptors.

The amount of water soluble substance to be added to the aqueous solution can vary within fairly wide limits, and a range from appr. 0.3 M up to the saturation concentration of the water soluble and surface tension increasing substance has been found suitable. An especially preferred range is 2 to 6 M, especially when the substance is a salt, such as sodium chloride.

According to an embodiment of the invention, the aqueous solution, the surface tension of which is measured, can be an aqueous solution of an amphiphilic substance, typically, but not limited to a drug, and especially a drug which is to diffuse through the blood-brain barrier, such as a drug for the treatment of disorders in the central nervous system (CNS).

According to a preferred embodiment of the invention, the amphiphilic substance is added to the aqueous solution dissolved in a solvent which is sufficiently water soluble, such as DMSO or a lower alcohol, such as methanol, dimethylformamide, toluene, or isopropanol. The concentration of the water soluble solvent in the aqueous solution is not very critical, a usable range being from 0.1 to 20% by volume of the solution. Good results have been obtained with amounts as low as 1% by volume. Lower amounts are naturally preferred because of less interference of the solvent with the measurement.

When an amphiphilic substance, for example dissolved in a water soluble solvent, is added to the aqueous solution, the substance partitions in the air/water interface, causing a decrease in the surface tension (increase in the surface pressure). By using in the aqueous solution, in addition, a substance which in itself causes an increase in the surface tension, it is possible to make the measurement more sensitive, i.e. to obtain a more marked and bigger change in the surface tension or surface pressure values when testing the amphiphilic substance for its surface activity, at smaller concentrations of the amphiphilic substance and using less water soluble solvent. The changes in surface pressure as a function of concentration are measured at low concentrations of substance, which typically are of the order of 0.1 nM to 10 M, preferably 0.1 nM to 10 mM.

The surface pressure, which is inversely proportional to the surface tension, can be measured for example by measuring the force applied to a sensor in the air/water interface. Such a sensor can be in the form of a thin platinum plate, such as a Wilhelmy plate, which is placed in the air/water interface. The change in surface pressure is evidenced as a change in the amount of liquid adhered to the plate. When the surface pressure of the liquid increases, the amount of water adhered to the plate decreases linearly, and vice versa. The surface of the sensor is wetted by the influence of the surface pressure, which is evidenced as an increase of the weight of the sensor or in the load applied to the sensor. The force applied to the sensor by the surface pressure makes the sensor move in the vertical direction. This force can be measured, for example, using a commercial microbalance.

An alternative construction for the sensor is in the form of a small diameter metal alloy wire probe, i.e. a so-called de Nouy ring.

By determining the surface tension or surface pressure as a function of the concentration of the substance to be tested, the effect of the substance on the surface pressure, i.e. the surface pressure or tension as a function of the concentration can be determined. The curve obtained by plotting the surface pressure as a function of the logarithm of the concentration of the substances allows the determination of a number of properties, including the interfacial area of the molecule, the air-water partition coefficient, and the critical micellar concentration, which contribute to the surface activity profile of the substances. This is as such known in the art, and described for example in the publication *J. Membrane Biol.* 165:201–211 (1998)), referred to above. In the following example, this is described in more detail.

EXAMPLE

In the example, DMSO was used as the preferred solvent for the drugs. The drugs were dissolved in DMSO in a concentration of 10 vol-% and 1 vol-%. Serial dilutions were done in DMSO in 96-well plates (Corning, N.Y., USA). Subsequently, 6 $\mu$l of these DMSO solutions were transferred into 55 $\mu$l of buffer (114 mM NaCl, 50 mM Tris-HCl, pH 8.0) or the same buffer containing 4 M of NaCl in the measurement cuvette (Kibron Inc., Helsinki, Finland). For compounds which do not dissolve sufficiently in DMSO, methanol can be used instead.

Surface activities can be measured using a multi-channel microtensiometer (MultiPi, Kibron Inc.) with an automated calibration, and measurement program. For calibration, the first well contained the buffer with the solvent. Surface tension was determined by the du Nouy technique using a small diameter metal alloy wire probe. Thirteen subsequent wells were measured in parallel on each of the channels. To minimise carry over, the highest drug concentration was in the last sample well. The error within one channel while measuring the surface tension of pure water varied between 0.12 to 0.34 mN/m. Error between different channels was 0.30 mN/m.

Figure 2:
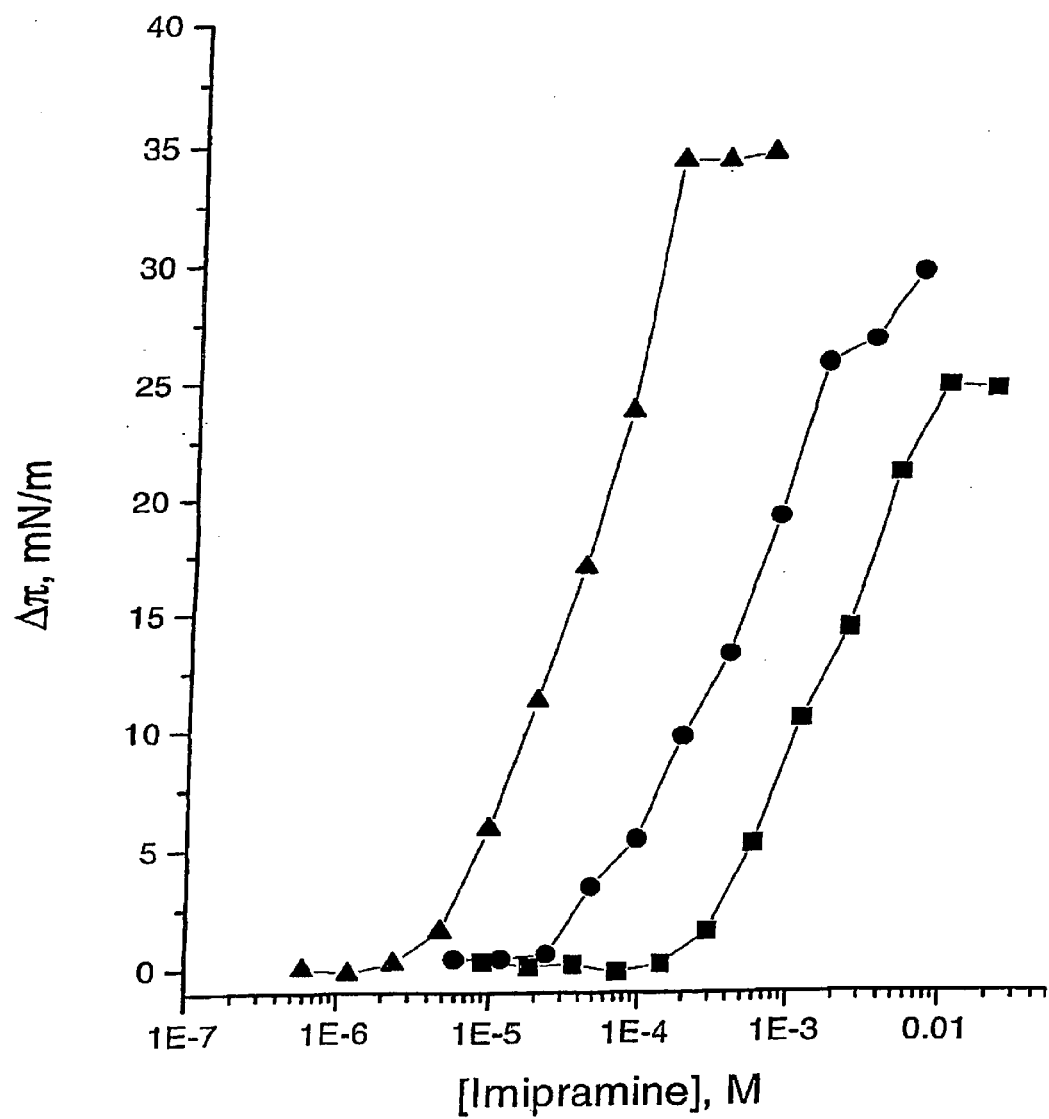
FIG. 2 is a similar graph as that of FIG. 1, but shows the surface pressure as a function of lnC for the drug imipramine, wherein the solutions correspond to those of FIG. 1.
Figure 3:
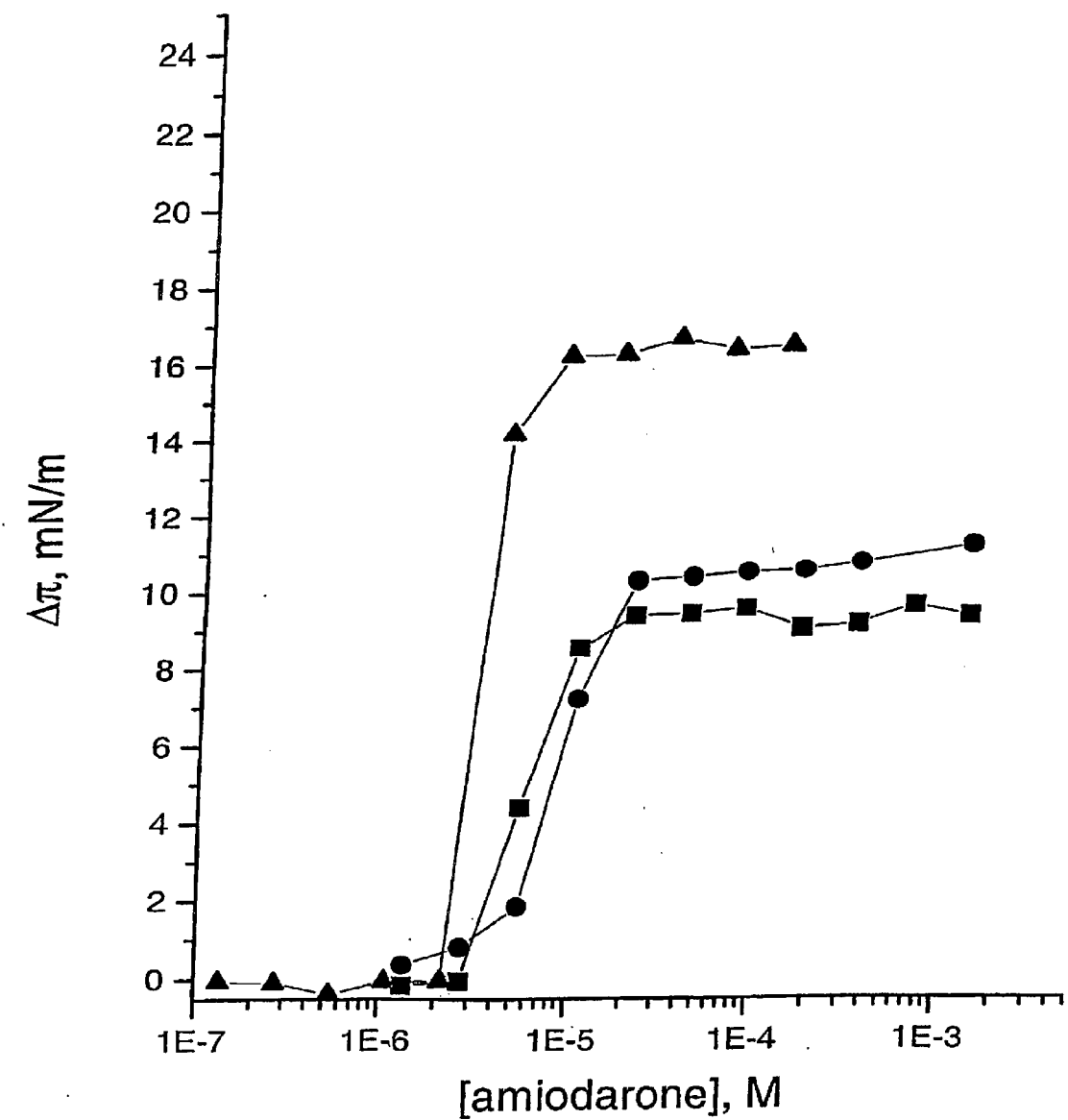
FIG. 3 is a similar graph as that of FIG. 1, but shows the surface pressure as a function of lnC for the drug amiodarone, wherein the solutions correspond to those of FIG. 1.

In this way, the surface activity profiles shown in the appended FIGS. 1–3 were obtained.

As is known, the adsorption of an amphiphile to the air-water surface decreases the surface tension, $\gamma$. The difference between surface tension for the aqueous solution, $\gamma o$, and the value measured for the drug solution, $\gamma$ yields the surface pressure, $\pi=\gamma o-\gamma$. Using Gibbs adsorption isotherm, the thermodynamics of this process are given by the equation:

$$d\gamma = -RT(N_A A_S)^{-1} dlnC = -RT\Gamma dlnC = -d\pi$$

where C is the concentration of the amphiphile, RT is the thermal energy, $N_A$ is Avogadro's number, and $A_s$ is the interfacial area of the amphiphile. By plotting the p vs. lnC a, linear slope is obtained. This slope corresponds to the surface excess concentration, $\Gamma\infty$. From these data $A_s$ is derived using the equation:

$$A_S = (N_A \Gamma_\infty)^{-1}$$

The air-water partition coefficient, $K_{aw}$ can be calculated from the measured data by fitting $\pi/C$ curve to obtain $\Gamma_\infty$ and using equation:

$$\pi = RT\Gamma_\infty ln(1+K_{aw}C)$$

The amphiphilicity index, $\Theta$, is obtained from CMC/$K_{aw}$, where CMC is the critical micellar concentration. CMC is obtainable from the plot as the concentration where the increase in surface pressure $\pi$ levels off, as depicted by the arrow in FIG. 1

As stated above, useful parameters for determining the ADME properties of a substance are i.a. the interfacial area $A_s$, the air-water partition coefficient $K_{aw}$ and the critical micellar concentration CMC, which parameters allow i.a. a determination of the amphiphilicity index of the substance which in turn provides a means to determine the ability of the substance to cross the blood-brain-barrier.

What is claimed is:

1. A method for determining the surface activity properties of an amphiphilic substance, the method including a step wherein the surface tension of an aqueous solution of said substance is measured at its air-water interface at a plurality of concentrations of said substance, determining the relationship between the surface tension and the concentration of the substance, and using the relationship so determined to predict the surface activity properties of the substance, characterized in that to the aqueous solution a water soluble substance, which increases the surface tension of the aqueous solution, is added in an amount to provide a concentration of 0.3 M up to the saturation concentration of said water soluble substance in said solution.

2. The method according to claim 1, characterized in that the substance, the surface activity properties of which are to be determined, is added to the aqueous solution dissolved in a sufficiently water soluble solvent.

3. The method according to claim 1 or 2, characterized in that the water soluble substance which increases the surface tension of the aqueous solution is a salt selected from the group consisting of alkali- or earth-alkaline metal salts, carboxylic acid salts, and is preferably a halide.

4. The method according to claim 3, characterized in that the water soluble substance is added in an amount to provide a 2 to 6 M concentration of said water soluble substance.

5. The method according to claim 4, characterized in that the water soluble substance is added in an amount to provide an approximately 4 M concentration of said water soluble substance.

6. The method according to claim 3, wherein the water soluble substance which increases the surface tension of the aqueous solution is sodium chloride.

7. The method according to claim 1 or 2, characterized in that the water soluble substance, which increases the surface tension of the aqueous solution, is selected from the group consisting of sugars and polyols, amino acids, choline, and betaine.

8. The method according to claim 2, characterized in that the water soluble substance is added in an amount to provide a 2 to 6 M concentration of said water soluble substance.

9. The method according to claim 8, characterized in that the water soluble substance is added in an amount to provide an approximately 4 M concentration of said water soluble substance.

10. The method according to claim 2, characterized in that the water soluble solvent comprises 0.1 to 20% by volume of the whole solution.

11. The method according to claim 2, wherein the sufficiently water soluble solvent is a lower alcohol.

12. The method according to claim 11, wherein the sufficiently water soluble solvent is methanol.

13. The method according to claim 2, wherein the sufficiently water soluble solvent is dimethylsulfoxide.

* * * * *